(12) United States Patent
Karwei

(10) Patent No.: US 9,381,034 B2
(45) Date of Patent: Jul. 5, 2016

(54) WATER JET SURGICAL INSTRUMENT

(75) Inventor: Dietmar Karwei, Ofterdingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 462 days.

(21) Appl. No.: 13/263,692

(22) PCT Filed: Mar. 10, 2010

(86) PCT No.: PCT/EP2010/001489
§ 371 (c)(1),
(2), (4) Date: Nov. 17, 2011

(87) PCT Pub. No.: WO2010/115499
PCT Pub. Date: Oct. 14, 2010

(65) Prior Publication Data
US 2012/0065656 A1 Mar. 15, 2012

(30) Foreign Application Priority Data
Apr. 8, 2009 (DE) .................. 10 2009 016 859

(51) Int. Cl.
*A61B 17/3203* (2006.01)
*B05B 1/12* (2006.01)
*B05B 1/34* (2006.01)

(52) U.S. Cl.
CPC ............ *A61B 17/3203* (2013.01); *B05B 1/12* (2013.01); *B05B 1/3415* (2013.01)

(58) Field of Classification Search
CPC .... B05B 1/341; B05B 1/3421; B05B 1/3426; B05B 1/3431; B05B 1/3442; B05B 1/3452; B05B 1/3468; B05B 1/3415; B05B 1/12; B05B 1/34; B05B 1/3405; B05B 7/10; B05B 7/1218; A61B 17/3203

USPC ........ 604/22, 70, 21; 239/698, 704, 697, 399, 239/402.5, 403, 404, 406–408, 11, 239/487–490, 492, 494–497, 329–332, 343, 239/382, 464, 466, 102.1, 142, 499, 590, 239/590.5, 509–515, 505, 518, 519, 521, 239/523, 524, 461, 463, 465–467, 480, 500, 239/502, 699, 701, 703, 383, 389–391, 385, 239/396, 489, 503, 507, 513, 514; 606/167, 606/159; 440/38, 44; 433/80; 417/65, 151, 417/158; 28/271; 73/504.06; 601/160; 165/908; 600/29, 30; 128/885; 222/226, 228

See application file for complete search history.

(56) References Cited

U.S. PATENT DOCUMENTS 2,751,252 A * 6/1956 Wahlin et al. .................. 239/489
4,014,318 A * 3/1977 Dockum et al. ................ 600/16
(Continued)

FOREIGN PATENT DOCUMENTS

DE      698 24 728 T2    8/2005
DE   10 2007 002 486 A1   7/2008
(Continued)

*Primary Examiner* — Jocelin Tanner
(74) *Attorney, Agent, or Firm* — Blank Rome LLP

(57) ABSTRACT

Water jet surgical instruments comprising a feed line for supplying fluid in one flow direction and one exit nozzle for ejecting the fluid in the form of a fine jet displaying a defined geometric opening configuration are known. In order to be able to widen the jet a fluid chamber is provided—viewed in the direction of flow—upstream of the exit nozzle. A disturbance device is provided in or on the fluid chamber, said disturbance device being able to generate a turbulent flow inside the fluid chamber.

13 Claims, 2 Drawing Sheets

(56) References Cited

U.S. PATENT DOCUMENTS

| | | | |
|---|---|---|---|
| 4,335,949 A * | 6/1982 | Kukucka et al. | 399/11 |
| 4,355,949 A * | 10/1982 | Bailey | 415/35 |
| 4,413,782 A * | 11/1983 | Platzer et al. | 239/380 |
| 4,585,177 A * | 4/1986 | Sugawara et al. | 239/590 |
| 5,135,482 A | 8/1992 | Neracher | |
| 5,620,414 A * | 4/1997 | Campbell, Jr. | 604/22 |
| 5,865,790 A | 2/1999 | Bair | |
| 5,944,686 A | 8/1999 | Patterson et al. | |
| 6,117,150 A | 9/2000 | Pingleton et al. | |
| 6,354,519 B1 * | 3/2002 | Kidooka et al. | 239/491 |
| 7,100,846 B2 * | 9/2006 | Pein | 239/483 |
| 7,513,877 B2 * | 4/2009 | Viola | 600/564 |
| 2002/0007143 A1 | 1/2002 | Gordon | |
| 2005/0279863 A1 * | 12/2005 | Malcolm | 239/461 |
| 2008/0132888 A1 | 6/2008 | Iida et al. | |
| 2008/0230632 A1 * | 9/2008 | Fenton et al. | 239/433 |
| 2008/0262302 A1 * | 10/2008 | Azarbarzin et al. | 600/114 |
| 2009/0140077 A1 * | 6/2009 | Lee et al. | 239/463 |

FOREIGN PATENT DOCUMENTS

| | | |
|---|---|---|
| DE | 10 2008 025 233 A1 | 12/2009 |
| EP | 0 691 183 A1 | 1/1996 |
| EP | 1 800 612 A1 | 6/2007 |

\* cited by examiner

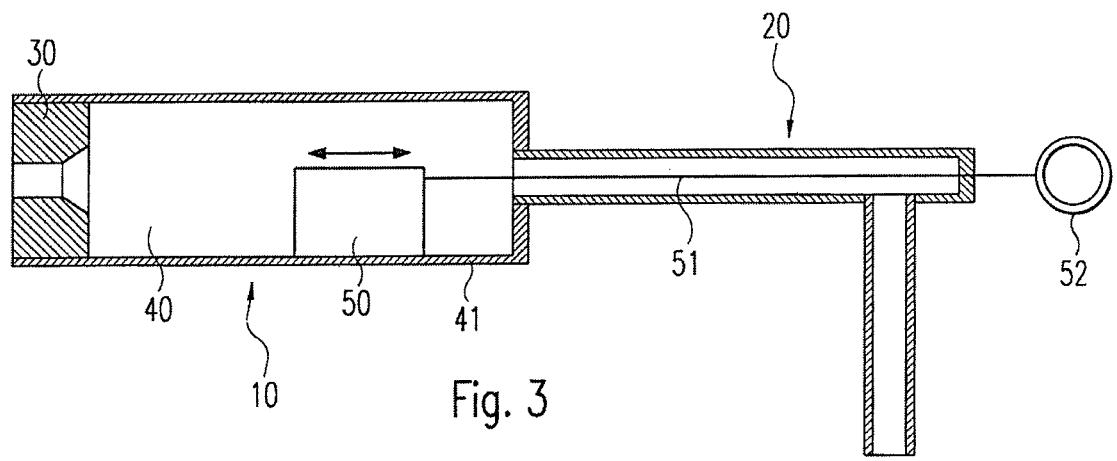
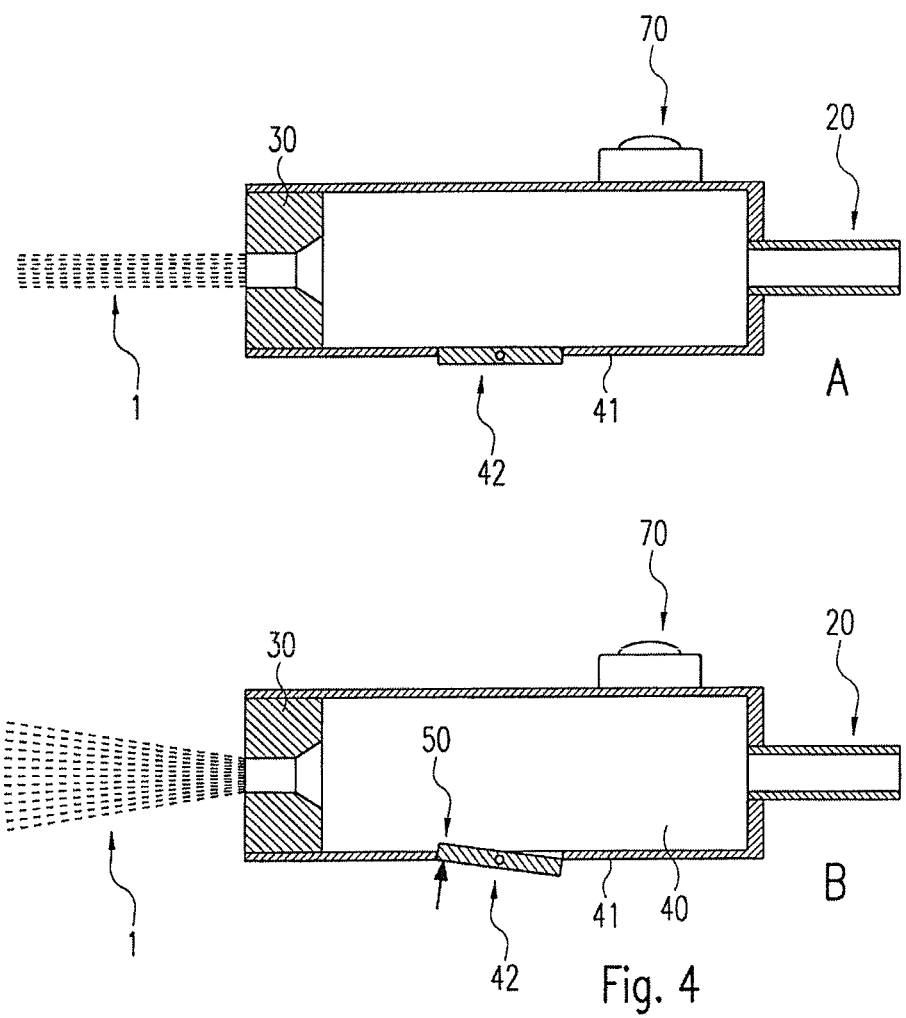

WATER JET SURGICAL INSTRUMENT

FIELD OF THE INVENTION

Embodiments of the invention relate to a water jet surgical instrument having control of the geometric configuration of its fluid jet using a simple design.

BACKGROUND

Water jet surgical devices are being increasingly used in surgery because their cutting or, better said, their separating behavior is different from the usual scalpels and alternative devices such as laser surgical or RF surgical apparatuses.

In particular, water jet surgical devices can be used for incisions that separate certain tissue types and leave others untouched (i.e., selective tissue separation).

Finally, such techniques are being increasingly used in endoscopic surgical procedures.

Such water jet surgical devices comprise a fluid reservoir and a fluid conveyor system for conveying the fluid through a pressure line from the fluid reservoir to a water jet surgical instrument that is connected to the water jet surgical device. The water jet surgical instrument itself comprises an ejection nozzle to eject the fluid in the form of a fine fluid jet.

In the resection of tissue, e.g., tumor tissue in the gastrointestinal tract, the water jet must leave the ejection nozzle bundled under high pressure. If—as in the aforementioned example application—the resection of the tumor tissue is limited to the mucosa, the tumor tissue should be ectomized as completely as possible and, if possible, in one session; this being possible with a fluid jet. In conjunction with this, however, there is a problem that the "bundled" fluid jet can result in a perforation of the muscularis propria. The consequence of such perforation is dangerous internal bleeding concealing the surgical site. Furthermore, considering other applications of water jet surgical devices, it is desirable to change the exit angle of the fluid jet such that inadvertent injuries caused by the surgeon do not occur or that other functions of the fluid jet are made possible (e.g., rinsing).

U.S. Pat. No. 5,944,686 discloses a surgical instrument for water jet surgery in which a cutting fluid jet is atomized via a deflecting surface and the exit angle of the fluid jet is changed. In doing so, this deflecting surface is arranged distally from the actual ejection nozzle.

German Publication DE 10 2007 002 486 A1 discloses a water jet surgical instrument in which a fluid jet having an essentially round cross-section impinges on a spoon-like impact surface and is converted there into a flattened water jet. In this case, the spoon-like surface is shaped as an elongated distal end of a suction pipe starting at this point, i.e., again, its location is distal to the ejection nozzle.

Consequently, until now, it has been unanimously suggested to provide special devices such as impact surfaces or deflecting surfaces to impart the fluid jet with a form deviating from the round cross-section or with another exit angle. However, such add-on devices interfere with the clear view of the surgical site and interfere with the work of the instrument itself because there is always another device downstream of the actual fluid dispensing element, the ejection nozzle, said device being in an unfavorable location for surgical work.

SUMMARY

An object of the embodiments of the invention is to provide a water jet surgical instrument that, using a simple design, allows a control of the geometric configuration of the fluid jet, without substantially worsening the handleability of the instrument.

This object is achieved with a water jet surgical instrument comprising a feed line for supplying fluid in one direction of flow, and an exit nozzle for ejecting the fluid in a jet having a defined geometric opening configuration, where, viewed in the direction of flow of the fluid, a fluid chamber is provided upstream of the exit nozzle and wherein a disturbance device is provided in or on the fluid chamber, said disturbance device being able to generate a turbulent flow inside the fluid chamber.

In the fluid chamber that is dimensioned to be sufficiently large and also symmetrical in design, the fluid flow is initially laminar. This means that, in the flow, the inertial forces predominate relative to the frictional forces at each point of the fluid chamber. When the fluid in such a form of flow reaches the ejection nozzle, a more or less fine fluid jet, said fluid jet being sharply contoured at least when exiting, will exit the ejection nozzle—provided that the geometric configuration of the nozzle is designed accordingly.

Surprisingly, it has now been found that the form of the exiting fluid jet changes such that the fluid jet will no longer exit as a fine jet as soon as the flow in the fluid chamber starts to become turbulent. Then, the fluid jet is widened more or less. This is particularly surprising because there is no interference with the actual fluid jet after leaving the ejection nozzle yet the flow—with a totally unchanged situation—is changed much farther upstream in the fluid chamber on leaving, or after leaving, the ejection nozzle. However, this provides the possibility of changing the flow behavior at a point of the flow that is much less disruptive for the user of the water jet surgical instrument.

To allow the flow in the fluid chamber to become turbulent, the geometric configuration of the fluid chamber is modified at any point such that the flow will become asymmetrical with respect to length, width and/or radius. As a result, the flow will become partially turbulent at that point. Here, the frictional forces and the inertial forces of the molecules will be predominant.

Considering a first preferred embodiment, the disturbance device comprises a body that can be surrounded or perfused by the flow, said body being arranged in the fluid chamber, in order to convert the laminar flow into a turbulent flow. Using an otherwise unchanged geometric configuration of the fluid chamber, it has been found that a stationary disturbance device results in an unvarying and repeatable widening of the fluid jet.

Considering another preferred embodiment, the disturbance device comprises a preferably flexible wall of the fluid chamber. By adjusting the form (cross-section) of the fluid chamber it is thus also possible to accomplish a reproducible widening of the jet.

The disturbance device may be permanently built into the fluid chamber or the fluid chamber may have unchangeable dimensions, whereby various water jet surgical instruments for various geometric configurations of the jet can be provided.

Considering a preferred embodiment, the disturbance device is designed to be adjustable in view of its position and/or geometric configuration to change the geometric opening configuration of the jet. The surgeon can then "shape" the fluid jet by an appropriate adjustment of the disturbance device such that said jet serves the surgeon's purposes. This can be accomplished, for example, with an actuation system for moving the disturbance device inside the fluid chamber. In the preferred embodiment, the actuation system comprises a push and pull element, in particular a wire, for moving the disturbance device inside the fluid chamber. In this case, the push and pull element is then connected to a handle that can be actuated by the surgeon.

Alternatively, the actuation system may also comprise a magnetic element for the application of a magnetic force to the disturbance device. In this case, a mechanical intervention in the fluid chamber is not necessary, so that a sealing of the actuation system is not necessary (which is beneficial because such sealing is not without problems considering the high pressures involved).

Preferably, the water jet surgical instrument is designed for insertion in a channel of an endoscope. Here, the advantages of the instrument are demonstrated in a particularly drastic manner when the disturbance device can be changed by the surgeon. The reason being that, in this case, an instrument change is particularly complicated; however, such a change need no longer be made because of the adjustability of the disturbance device.

BRIEF DESCRIPTION OF THE DRAWINGS

Hereinafter, preferred embodiments of the invention will be explained in greater detail with reference to the drawings, in which:

FIG. 3 illustrates another embodiment of the invention based on a disturbance device of FIG. 1 or FIG. 2; and FIGS. 4A and 4B illustrate another embodiment of the invention, with the disturbance device illustrated in two positions.

DETAILED DESCRIPTION

In the following description the same reference signs are used for parts that are the same or for parts that have the same function.

Figure 1:
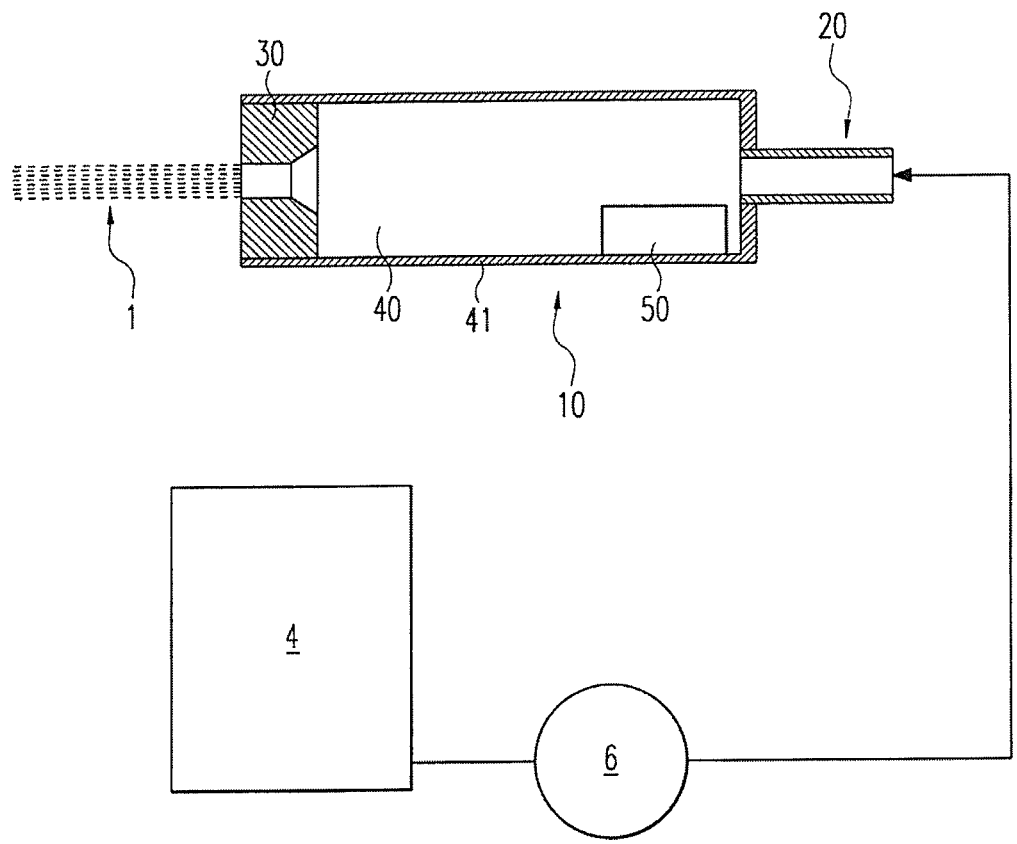
FIG. 1 is a schematic diagram of a water jet surgical device, with a disturbance device in a first position.

FIG. 1 shows an embodiment of the invention where a water jet surgical instrument is connected with a fluid reservoir 4 via a feed line 20 and a pump 6. A fluid chamber 40 is interposed between the feed line 20 and an ejection nozzle 30, said fluid chamber 40 having an exterior wall. In the illustrates embodiment, the fluid chamber 40 is dimensioned such that an essentially laminar flow of the fluid from the fluid reservoir 4 is generated in the fluid chamber 40 when said fluid is ejected through the ejection nozzle 30. The ejection nozzle 30 is configured such that, with a laminar flow in the fluid chamber 40, an essentially "cylindrical" fluid jet 1 is formed. With an appropriately high pressure, such a fluid jet 1 can be used to perform the desired treatment of the tissue, namely a selective cutting of said tissue.

Figure 2:
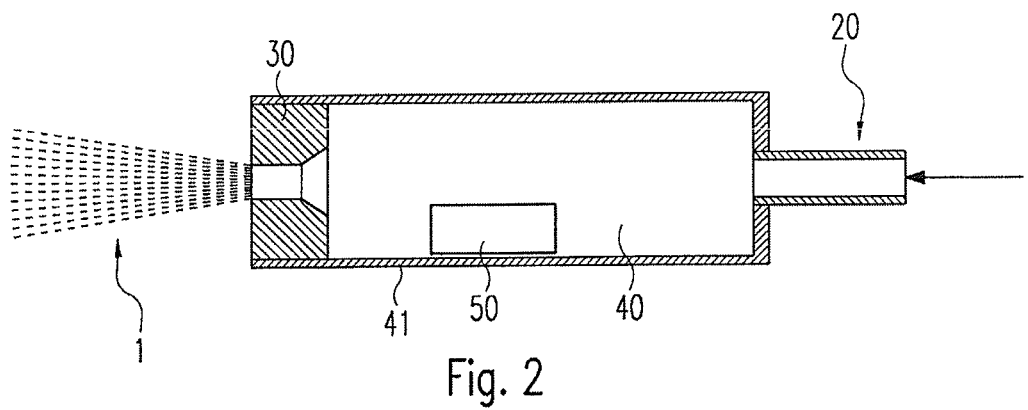
FIG. 2 illustrates the components of the water jet surgical instrument of FIG. 1, said components being essential in this case, with a disturbance device in a position that has been changed relative thereto.

Arranged in the fluid chamber 40 is a disturbance device 50 that is configured as a beveled body in the exemplary embodiment of FIG. 1; said disturbance device 50—when moved in the direction of the ejection nozzle 30 as shown in FIG. 2—converts the initially laminar flow in the fluid chamber 40 into a turbulent flow because the beveled body is surrounded by the fluid stream and said fluid stream is "broken" on the edges of disturbance device body. If the situation as shown in FIG. 2 exists, a turbulent flow exists in the fluid chamber 40 just upstream of the ejection nozzle 30. Due to this turbulent flow, the fluid jet 1 is now widened as is shown in FIG. 2.

Because the type of flow (laminar/turbulent) is changed upstream of the ejection nozzle 30, it is possible to influence the geometric configuration of the fluid jet 1. Consequently, a set of water jet surgical instruments 10 in which the disturbance devices 50 are provided at various locations (or in various forms) in the fluid chamber 40 can be made available to the surgeon. As a result, the fluid jet 1 has one or another geometric form, i.e., bundled or fanned.

The embodiment shown in FIG. 3 is different from that of FIGS. 1 and 2 in that the disturbance device 50 can be moved inside the fluid chamber 40, as is indicated by the double arrow. To accomplish this, a push and pull element 51 is provided, said element potentially being a stiff wire. This push and pull element 51 is moved out of the feed line 20 via a seal and has a first handle 52 on one end. Using this handle 52, the surgeon can adjust the geometric form of the fluid jet 1 during surgery when the surgeon moves the disturbance device 50. This embodiment is advantageous for open surgery; it is also particularly advantageous in endoscopic applications because an instrument change to replace a bundled jet with a widened jet is particularly advantageous.

In the embodiment shown in FIGS. 4A and 4B, the disturbance device is provided in the exterior wall 41 of the chamber 40 via a movable exterior wall section 42. If the orientation of the exterior wall section 42 is changed, i.e., the geometric configuration of the fluid chamber 40 is changed, it is also possible to generate a turbulent flow inside the fluid chamber 40 and thus widen the fluid jet 1. This is shown by FIG. 4A (laminar flow=bundled jet) and FIG. 4B (turbulent flow=widened fluid jet). This movable exterior wall section 42 (representing the disturbance device 50) is now supported such that—when it is being tilted (see direction of the arrow in FIG. 4B)—one part of the exterior wall section 42 enters the fluid chamber 40, whereas another part of the movable exterior wall section 42 tilts farther out of the fluid chamber 40. Consequently, a neutralization of the forces acting on the exterior wall section 42 is achieved due to the fluid pressure 40 inside the chamber.

In addition to the movable exterior wall section 42 as the actuation system, an actuation switch 70 is also provided, so that the water jet surgical instrument shown in FIGS. 4A and 4B can be envisaged overall as a handleable component for open surgery.

It been shown hereinabove that the embodiments of the invention also relate to a method for changing the form of the exiting fluid jet in a water jet surgical instrument in that a laminar flow present upstream of the ejection nozzle is converted from a laminar flow into a turbulent flow.

The invention claimed is:

1. A water jet surgical instrument comprising:
   a feed line for supplying fluid in one direction of flow;
   an ejection nozzle for ejecting the fluid in a jet having a defined geometric opening configuration;
   a fluid chamber provided upstream of the ejection nozzle, viewed in the direction of flow of the fluid; and
   a disturbance device provided in or on a wall of the fluid chamber and extending only part way across the fluid chamber so as not to contact an opposite wall of the fluid chamber, said disturbance device being able to generate a turbulent flow inside the fluid chamber,
   wherein a portion of the disturbance device directly connected to the wall moves from a first position to a second position.

2. A water jet surgical instrument as in claim 1, wherein the disturbance device comprises a body that can be surrounded by the flow.

3. A water jet surgical instrument as in claim 1, wherein the disturbance device is provided in the fluid chamber and a position of the disturbance device is designed to be adjustable to change the geometric opening configuration of the fluid jet.

4. A water jet surgical instrument as in claim 1, wherein a geometric configuration of the disturbance device is designed to be adjustable to change the geometric opening configuration of the fluid jet.

5. A water jet surgical instrument as in claim 1, wherein an amplitude of the turbulence in the turbulent flow increases as the disturbance device is moved in a down-stream direction.

6. A water jet surgical instrument as in claim 1, wherein an amplitude of the turbulence in the turbulent flow increases as the disturbance device extends farther into the fluid chamber.

7. A water jet surgical instrument as in claim 1, wherein the water jet surgical instrument is capable of being inserted in a channel of an endoscope.

8. A method of changing a form of a fluid exiting a fluid jet of a water jet surgical instrument, said method comprising:
providing a laminar flow of fluid in a fluid chamber of the instrument, wherein said fluid chamber is symmetrical and includes a uniform diameter which is larger than that of an upstream feed line and a downstream ejection nozzle, as viewed in the direction of flow of the fluid; and
creating a turbulent flow from the laminar flow using a disturbance device positioned in or on a wall of the fluid chamber and upstream of the ejection nozzle, as viewed in the direction of flow of the fluid, the disturbance device extending only part way across the fluid chamber so as not to contact an opposite wall of the fluid chamber, wherein a portion of the disturbance device directly connected to the wall moves from a first position to a second position.

9. The method of claim 8, wherein a position of the disturbance device is altered by an operator of the water jet surgical device.

10. The method of claim 8, wherein the disturbance device is formed as part of a wall of the fluid chamber and a position of the disturbance device is altered by an operator of the water jet surgical device using a switch on the instrument.

11. The method of claim 8, wherein the creating a turbulent flow from the laminar flow comprises moving the disturbance device a down-stream direction.

12. The method of claim 8, wherein the creating a turbulent flow from the laminar flow comprises extending the disturbance device farther into the fluid chamber.

13. The method of claim 8, wherein the water jet surgical instrument is capable of being inserted in a channel of an endoscope.

* * * * *